US008519447B2

(12) United States Patent
Zeun

(10) Patent No.: US 8,519,447 B2
(45) Date of Patent: Aug. 27, 2013

(54) ION SENSITIVE SENSOR WITH MULTILAYER CONSTRUCTION IN THE SENSOR REGION

(75) Inventor: Hendrik Zeun, Chemnitz (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 20 days.

(21) Appl. No.: 13/389,627

(22) PCT Filed: Jul. 21, 2010

(86) PCT No.: PCT/EP2010/060515
§ 371 (c)(1), (2), (4) Date: Feb. 9, 2012

(87) PCT Pub. No.: WO2011/018310
PCT Pub. Date: Feb. 17, 2011

(65) Prior Publication Data
US 2012/0139011 A1    Jun. 7, 2012

(30) Foreign Application Priority Data

Aug. 12, 2009  (DE) .................. 10 2009 028 486

(51) Int. Cl.
| G01N 27/403 | (2006.01) |
| H01L 27/14 | (2006.01) |
| H01L 21/00 | (2006.01) |
| H01L 21/336 | (2006.01) |

(52) U.S. Cl.
USPC ............ 257/253; 257/414; 257/E29.255; 257/E29.166; 257/E29.242; 257/E27.06; 438/10; 438/49; 438/197

(58) Field of Classification Search
None
See application file for complete search history.

(56) References Cited

U.S. PATENT DOCUMENTS

| 4,305,802 A * | 12/1981 | Koshiishi .................. 204/418 |
| 2003/0186262 A1* | 10/2003 | Cailloux ...................... 435/6 |
| 2009/0014757 A1* | 1/2009 | Takulapalli et al. .......... 257/253 |

FOREIGN PATENT DOCUMENTS

| DE | 4232532 | 4/1994 |
| DE | 10 2005008051 A1 | 8/2006 |
| DE | 102009002060 A1 | 10/2010 |
| WO | WO 2005 073706 A1 | 8/2005 |
| WO | WO 2005073706 A1 * | 8/2005 |

OTHER PUBLICATIONS

German Search Report for German Patent Appl. 102009028486.9.
International Search Report.
H. Gruger et al., "High quality r.f. sputtered metal oxides ($Ta_2O_5$, $HfO_2$) and their properties after annealing", Thin Solid Films, Elsevier-Sequoia S.A., Lausanne, Switzerland Jan. 2004.
English translation of the IPR.

* cited by examiner

*Primary Examiner* — Julio J Maldonado
*Assistant Examiner* — Harpreet Singh
(74) *Attorney, Agent, or Firm* — Bacon & Thomas, PLLC

(57) ABSTRACT

An ion sensitive sensor having an EIS structure, including: a semiconductor substrate, on which a layer of a substrate oxides is produced; an adapting or matching layer, which is prepared on the substrate oxide; a chemically stable, intermediate insulator, which is deposited on the adapting or matching layer; and an ion sensitive, sensor layer, which is applied on the intermediate insulator. The adapting or matching layer differs from the intermediate insulator and the substrate oxide in its chemical composition and/or structure. The adapting or matching layer and the ion sensitive, sensor layer each have an electrical conductivity greater than that of the intermediate insulator. There is an electrically conductive connection between the adapting or matching layer and the ion sensitive, sensor layer.

24 Claims, 2 Drawing Sheets

ION SENSITIVE SENSOR WITH MULTILAYER CONSTRUCTION IN THE SENSOR REGION

TECHNICAL FIELD

The present invention relates to an ion sensitive sensor with an electrolyte insulator semiconductor (EIS) structure, especially an ion sensitive field effect transistor (ISFET) or an ion sensitive sensor with an EIS structure and light based measured value registering.

BACKGROUND DISCUSSION

A sensor having an EIS structure includes a semiconductor substrate, on which an insulator is arranged, which is supplied with an electrolyte in measurement operation.

ISFETs are established examples of sensors with an EIS structure, wherein, in this case, the insulator forms the ion sensitive gate insulator of a field effect transistor.

In sensors called LAPS (light addressable potentiometric sensors), photoelectrons are produced in the semiconductor material of an EIS structure by means of a modulated light signal, wherein the generation of photoelectrons depends, in turn, on the electrolyte properties. A basic description of LAPS is given by Hafeman et al. in "Light addressable potentiometric sensor for biochemical systems", *Science* 240 (1988) 1182-1185.

ISFETs are more established and better examined than other EIS structures. Therefore, in the following description of the problems in the state of the art, reference is essentially made to ISFETs, wherein it is inherent that these problems are correspondingly given for other sensors with an EIS structure.

Ion sensitive field effect transistors (ISFET) are applied for measuring ion concentrations or special substance concentrations in solutions of different compositions and conductivities. ISFETs are applied for the continuous verification of concentrations in environmental monitoring, in industrial process monitoring, in the foods industry and in biochemical/medical technology. Such applications especially depend on highly precise registration of concentration, quick start-up and minimal long time drift of the sensor, plus an acceptable price.

German patent application 10 2009 002060 describes an ISFET and a LAPS distinguished by special media resistance. Reference is made to the detailed discussion of the state of the art there.

Patent application 10 2009 002060 starts with the problem that $Ta_2O_5$ ion sensitive layers, which have favorable properties as regards sensitivity and linearity, are especially unstable in the presence of alkaline media with a pH>10, which leads to such media diffusing through the ion sensitive layer; such media can damage or destroy deeper lying layers. Media resistance is achieved according to the teachings of patent application DE 10 2009 002060 by a multilayer construction, in that an essentially crystalline insulation layer is arranged under the ion sensitive layer contacting the media. More exactly, the ion sensitive sensor having an EIS structure disclosed therein includes a semiconductor substrate, on which a layer of a substrate oxide is produced; an adapting or matching layer, which is prepared on the substrate oxide; a chemically stable, intermediate insulator, which is deposited on the adapting or matching layer; and a sensor layer, which comprises tantalum oxide or tantalum oxynitride, which is applied on the intermediate insulator; wherein the intermediate insulator comprises hafnium oxide or zirconium oxide or a mixture of these oxides, and wherein the adapting or matching layer differs from the intermediate insulator and the substrate oxide in its chemical composition and/or in its structure. The adapting or matching layer can comprise, for example, tantalum oxide or tantalum oxynitride.

The ion sensitive layer and the adapting or matching layer of the sensor of DE 10 2009 002060 have an electrical conductivity, which is certainly small but exceeds the conductivity of the intermediate insulator by orders of magnitude. In this respect, the ion sensitive layer and the adapting or matching layer form the electrodes of a capacitor with the intermediate insulator as the dielectric. This can lead, in given cases, to charging and, therewith, potential differences between the ion sensitive layer and the adapting or matching layer, which can effect a variable shifting of the working point of the ion sensitive sensor since charges depend on temperature and type of medium. Depending on the extent of the effect, a shifting of the working point can mean a considerable degradation of the ion sensitive sensor.

SUMMARY OF THE INVENTION

Considering the above described problems, it is an object of the present invention to provide a media resistant, ion sensitive sensor having an EIS structure, for example, an ISFET sensor or an ion sensitive LAPS, which overcomes the described disadvantages of the state of the art.

According to the invention, the object is achieved by an ion sensitive sensor with an EIS structure comprising a semiconductor substrate, on which a layer of a substrate oxide is produced, an adapting or matching layer, which is prepared on the substrate oxide, a chemically stable, intermediate insulator, which is deposited on the adapting or matching layer, and an ion sensitive, sensor layer, which is applied on the intermediate insulator, wherein the adapting or matching layer differs from the intermediate insulator and the substrate oxide in its chemical composition and/or in its structure.

The adapting or matching layer and the ion sensitive, sensor layer each have an electrical conductivity greater than that of the intermediate insulator, wherein, according to the invention, there is an electrically conductive connection between the adapting or matching layer and the ion sensitive, sensor layer.

The conductive connection preferably extends in the direction of the layer sequence between the adapting or matching layer and the ion sensitive, sensor layer.

The conductive connection can comprise especially the material of the adapting or matching layer, the material of the ion sensitive, sensor layer or a metal.

In a further development of the invention, the intermediate insulator is surrounded laterally by a conductive intermediate layer, which forms the conductive connection extending between the adapting or matching layer and the ion sensitive, sensor layer.

In another further development of the invention, the conductive connection comprises conductive channels, which extend through the intermediate insulator.

In a further development of the invention, the conductive connection is arranged in a lateral region of the ion sensitive sensor, which lies outside of the region, whose surface has the ion sensitive, sensor layer and which is in contact with the measured medium. In other words, a laterally traversing layer of the intermediate insulator is arranged under the total surface section of the ion sensitive, sensor layer, which is in contact with the measured medium.

In a further development of the invention, the ion sensitive, sensor layer comprises tantalum oxide or tantalum oxynitride.

In a further development of the invention, the intermediate insulator comprises hafnium oxide or zirconium oxide or a mixture of these oxides.

The substrate oxide, the adapting or matching layer, the intermediate insulator and the ion sensitive, sensor layer together form the insulator of the EIS structure.

In measurement operation, the sensor layer of the insulator can be contacted by a measured medium, wherein the measured medium is the "E" in the EIS structure due to its electrolytic properties.

The sensor having an EIS structure of the invention can especially comprise an ISFET sensor, e.g. a pH ISFET sensor, or a LAPS.

In a further development of the invention, the adapting or matching layer comprises at least one material selected from the group of materials consisting of hafnium oxide silicate, zirconium oxide silicate, mixtures of hafnium oxide zirconium oxide silicate, hafnium oxynitride silicate, and zirconium oxynitride silicate, mixtures of hafnium oxynitride zirconium oxynitride silicate, hafnium oxide, tantalum oxide, tantalum oxynitride, and tantalum hafnium oxynitride, mixtures of tantalum hafnium oxide silicate, and mixtures of tantalum hafnium oxynitride silicate, hafnium lanthanum oxide, hafnium lanthanum oxynitride, hafnium ceroxide and hafnium cerium oxynitride.

In a further development of the invention, the substrate oxide has a layer thickness of 2.5 nm to 150 nm, especially not less than 10 nm and no more than 90 nm.

In a further development of the invention, the adapting or matching layer has a layer thickness of 1 nm to 135 nm, especially not less than 5 nm and no more than 40 nm.

According to a further development of the invention, the intermediate insulator has a layer thickness of 20 nm to 200 nm, especially not less than 30 nm and no more than 170 nm, preferably not less than 50 nm and no more than 150 nm.

According to a further development of the invention, the sensor layer has a layer thickness of 10 nm to 200 nm, especially no more than 100 nm, and preferably no more than 50 nm.

According to a further development of the invention, the substrate comprises silicon, especially n-silicon.

According to a further development of the invention, the sensor having an EIS structure includes an ISFET, a p-channel field effect transistor, or an n-channel field effect transistor in a p-well.

According to a further development of the invention, the adapting or matching layer between the substrate oxide and the intermediate insulator has a transition from an amorphous structure to a nanocrystalline structure.

According to a further development of the invention, the intermediate insulator has a polycrystalline structure, especially a nanocrystalline structure.

According to a further development of the invention, the sensor layer has an amorphous structure, a partially crystalline structure or a polycrystalline structure, especially a nanocrystalline structure.

The method of the invention for manufacture of an ion sensitive field effect transistor of the invention includes preparation of the layer sequence described, wherein the intermediate insulator is especially deposited as a crystalline structure or as a high density amorphous or partially crystalline structure.

According to a further development of the invention, the intermediate insulator and sensor layer are together annealed, and the crystallinity set, by tempering.

According to a further development of the invention, the thickness of the substrate oxide is increased by tempering, wherein the layer thickness can be controlled by means of a controlled tempering and therefrom the sensor parameter, which is dependent on the thickness, can be specifically set.

According to a further development of the invention, metal oxides, metal oxynitrides, metal oxide silicates, and metal oxynitride silicates are applied by sputtering, electron beam evaporation or chemical vapor deposition technology.

According to a further development of the invention, metals, metal nitrides, metal silicides, and metal nitride silicides are applied by sputtering, electron beam evaporation or chemical vapor deposition technology and oxidized in a subsequent step.

According to a further development of the invention, crystalline deposition occurs at high particle energies on unheated substrates.

According to another further development of the invention, crystalline deposition on substrates occurs at temperatures higher than 250° C., wherein also in this case the crystalline deposition can occur at high particle energies.

Advantages and aspects of the invention and its further developments are summarized in the following.

The requirement of high chemical stability excludes the same layer material from being able to undertake a pH sensor task with sufficient linearity and low hysteresis. At the same time, its pH sensitivity must be sufficiently exact at extreme pH values so that the sensor is not immediately unsuitable in these corrosive solutions at high temperatures, even though holes or gaps are etched into the pH sensor layer and the hydrated surface zone grows.

A chemically stable layer must be, as much as possible, a self contained, highly dense material. A relatively thick layer of a highly dense, chemically stable material does not, however, have as good adhesion as the oxidized silicon wafers on a substrate base if the wafers are exposed to different temperature loadings in the semiconductor process. The silicon wafer itself must be oxidized so that the field effect transistor receives stable parameters. This substrate oxide $SiO_2$ simultaneously serves as a protective layer against the diffusion of metal ions from the overlying layers and electrically insulates these from the metal oxides, whose electrical insulating effect decreases under SIP conditions. Since the oxide of silicon has a very small dielectric constant, its layer thickness is preferably limited.

Since the sensor structure is exposed to electrochemical stress, the applied materials must be as redox stable as possible. The required combination of a plurality of layers should especially occur in such a manner that the grain boundaries of the metal compounds do not propagate directly from the surface to the $SiO_2$, set the $SiO_2$ under mechanical stress or even crack the $SiO_2$.

Highly dense, crystallinely deposited metal oxides, for example, $HfO_2$, having a high dielectric constant and a sufficient pH sensitivity, are distinguished by a very high chemical resistance, especially in strongly alkaline, measured media, as well as at high temperatures, whereby they are very well suited as an intermediate insulator under the pH-linear sensor layer and significantly lengthen the lifetime of the sensor. In any event, materials with a high dielectric constant show lower electrical leakage currents at the same effective insulator thickness. The stability of the crystallinely deposited material is so high that a shared tempering with the overlying and underlying layers does not lead to mixing and thereby does not lead to disturbances in the layers. Once crystallinely deposited, the structure scarcely changes when the temperature of the layer is increased. A structural change would first occur in the nearest lying phase transition, which, however, does not occur under usual conditions.

BRIEF DESCRIPTION OF THE DRAWINGS

The invention will now be explained based on an example of an embodiment illustrated in the drawing, the figures of which show as follows.

DETAILED DISCUSSION IN CONJUNCTION WITH THE DRAWINGS

Figure 1:
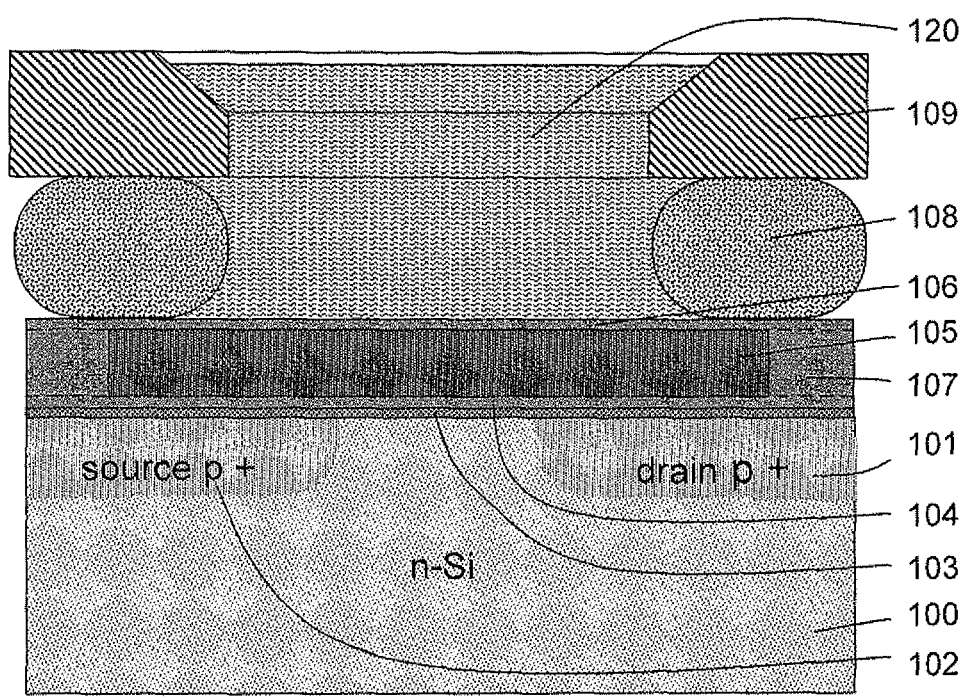
FIG. 1 is a schematic longitudinal section through a pH ISFET sensor of the invention.

FIG. 1 shows a longitudinal section of an ISFET sensor chip of the invention. Multiple chips, each having an area of about $3.5 \times 3.5$ mm$^2$, are manufactured all together in a semiconductor line on 150 mm silicon wafers. Separated chips are adhered on suitable substrates, contacted and incorporated into complete measuring systems by means of appropriate assembly methods. For example, immersion electrodes to measure pH are produced from the chips/boards.

The ISFET sensor of the invention essentially has the following structure. A substrate oxide 103 on a silicon substrate 100 forms the gate oxide and stabilizes the field effect, which is induced by a multilayer stack composed of sensor layer 106, intermediate insulator 105, adapting or matching layer 104 and substrate oxide 103, due to contact of a measured solution 120. The field effect enables a channel current between source 102 and drain 101, when an electrical potential difference is set between source 102 and drain 101 by an electrical contacting of source 102 and drain 101. The action of the field effect transistor can also be controlled by electrical contacting of the silicon bulk 100. An electrically conductive connection is produced between sensor layer 106 and adapting or matching layer 104; in the example of an embodiment the electrically conductive connection comprises the material of the sensor layer.

The adapting or matching layer 104 beneath the high density intermediate insulator 105 improves the adhesion of the double layer stack of intermediate insulator 105/pH sensor layer 106, interrupts grain boundary propagation toward substrate 100 and therewith lengthens the lifetime of the sensor. The adapting or matching layer 104 also optimizes the mechanical stress in the multilayer stack. Adapting or matching layer 104 structurally and electrically eases the otherwise abrupt structural transition from $SiO_2$, which remains amorphous even at very high temperatures, to the crystalline metal oxide $HfO_2$ of intermediate insulator 105.

In order to prepare the lateral structure of the conductive connection 107 surrounding intermediate insulator 105 according to a first method of manufacture, either the lateral region for the intermediate insulator or the lateral region for the conductive connection is first masked with a first mask before then the respectively other region is prepared. After its preparation the first mask is removed, the lateral region already prepared is masked with a second mask, and the missing region is prepared. Then the second mask is also removed and the ion sensitive, sensor layer is prepared across the top of both the intermediate insulator 105 and the conductive connection 107.

In order to prepare the lateral structure of conductive connection 107 surrounding intermediate insulator 105, according to a second method of manufacture, either the intermediate insulator or the conductive connection is first prepared in a continuous layer, in which then the lateral region for the respectively other structure is etched out and, after masking the already existing structure, the other structure is then deposited. After its preparation, the mask is removed and the ion sensitive, sensor layer is prepared.

As a result, all properties required for the chemically resistant and SIP stable pH sensor are acquired by producing multiple layers, especially a triple layer, on the substrate oxide, for example, $SiO_2$.

The triple layer arises through the insertion of the matching layer between substrate oxide 103 $SiO_2$ and the double layer, intermediate insulator 105 and pH sensor layer 106. The substrate oxide 103 is 25 to 1500 angstroms thick.

Adapting or matching layer 104 can comprise metal oxide silicate compounds, separately produced metal oxides or oxynitrides, or metal oxynitride silicates, which with their specific structures serve as a structure matching for intermediate insulator 105. Adapting or matching layer 104 is also difficult to crystallize even at higher process temperatures and can have an amorphous to crystalline structure. Adapting or matching layer 104 is preferably a specially structured $Ta_2O_5$ or an Hf or Zr silicate compound having a thickness of 10 to 1350 angstroms.

The intermediate insulator 105, preferably $HfO_2$, is deposited in its manufacture in crystalline form. This happens either by chemical vapor deposition processes with a substrate temperature of more than 250° C. or through PVD processes with high particle energy either at room temperature or likewise with a substrate temperature of more than 250° C., then, however, with somewhat lower particle energies. $ZrO_2$, $TiO_2$, oxides of the 3rd group of the periodic system and rare earth metal oxides or mixtures of these can be applied instead of $HfO_2$. The intermediate insulator 105 is preferably 200 to 2000 angstroms thick.

Deposited on crystalline intermediate insulator 105 is sensor layer 106, preferably amorphous or partially crystalline $Ta_2O_5$ of 100 to 2000 angstroms thick, which, together with the other layers and the substrate at high temperatures, is crystallized by means of special gases and gas mixtures, annealed and solidly connected with intermediate insulator 105. In such case, the surface area of the tantalum oxide increases and the desired small hysteresis with the high pH linearity is achieved.

By using tempering processes with oxidizing gases, the substrate oxide 103 can be reached through the metal oxides, such that the thickness of the substrate oxide 103 can be increased to achieve desired thicknesses. This substrate surface tuning can occur through oven processes at temperatures greater than 750° C. over a longer period of time (>30 min) or in a matter of seconds through RTA processes at temperatures up to 1150° C. A combination of both processes is desirable or necessary for targeted annealing near the surface coupled with simultaneous deep-reaching oxidation.

According to the invention, adapting or matching layer 104, intermediate insulator 105, and pH sensor layer 106 are deposited by sputtering the metals or metal oxides by means of $Ar/O_2$ or by CVD and are produced and conditioned through tempering in oxidizing and reducing gases. The heat treatments extend from 1000° C. to 400° C.

Through the application of metal oxide components, which are porous or conductive for oxygen ions at high temperatures and have high dielectric constants, the entire layer stack can in a single step be ridded of oxygen vacancies and readjusted as regards sensor working point.

It is essential that the region of ion sensitive, sensor layer 106, which is to be exposed to measured medium 120 in measurement operation, be bordered by a sealing arrangement 108, 109 in a manner such that no conductive connection through the intermediate insulator 105 is located under such region.

Figure 2:
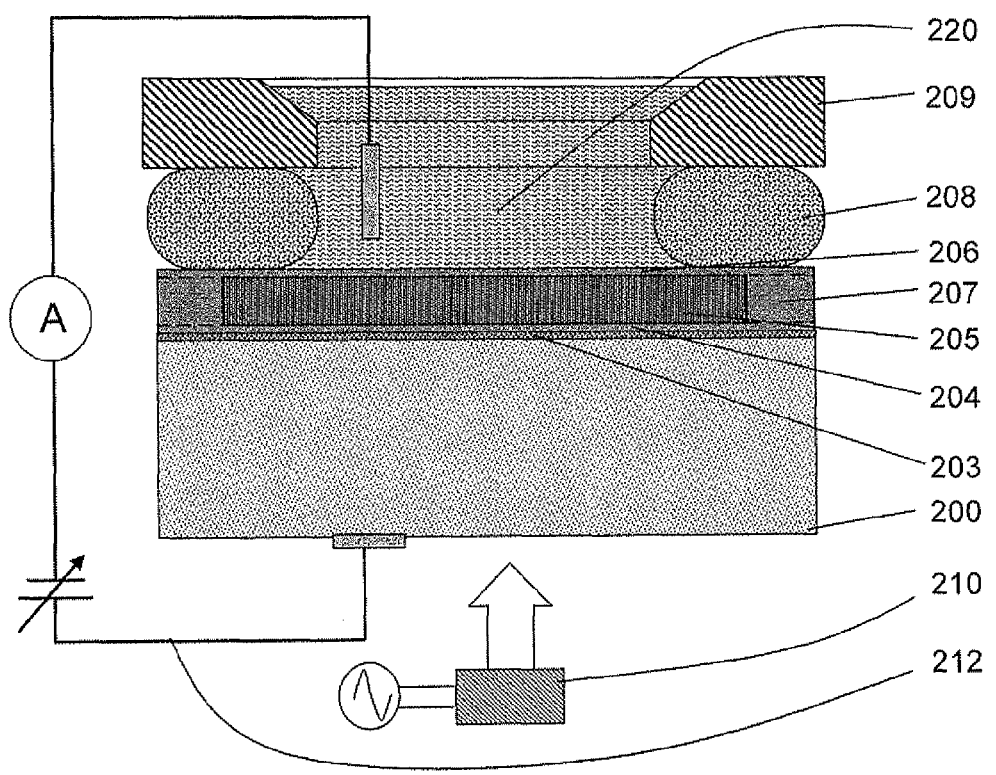
FIG. 2 is a schematic longitudinal section through a LAPS of the invention.

The light addressable potentiometric sensor (LAPS) shown in FIG. 2 includes a silicon substrate 200, on which a layer sequence 203 to 206 is prepared, which includes a substrate oxide 203, an adapting or matching layer 204, an intermediate insulator 205, and a sensor layer 206. Intermediate insulator 205 is surrounded by an annular electrical connection 207 to prevent potential shifts between adapting or matching layer 204 and sensor layer 206; annular electrical connection 207 extends between adapting or matching layer 204 and sensor layer 206. The region for contact with a medium 220 is laterally bordered by a sealing arrangement 208, 209.

As regards the chemical, structural and morphological properties of the layer sequence of the LAPS of the invention, the explanations for the same named layers of the ISFET sensor according to the invention correspondingly hold.

The LAPS of the invention furthermore includes a modulatable (laser-) light source 210 for generating photoelectrons in the silicon substrate. The modulated photocurrent registered by a measurement circuit 212 between a measured medium 220, which is supplied to sensor layer 206 of the LAPS, and silicon substrate 200 is a function of the ion concentration of the measured medium, for example, the pH value.

Literature

/1/ "Chemical sensitivity of an ISFET with $Ta_2O_5$ membrane in strong acid and alkaline solutions", P. V. Bobrov, et. al., Leningrad State University USSR, Sensors and Actuators B 3 (1991) 75-81.

/2/ "The pH-sensing properties of tantalum pentoxide films fabricated by metal organic low pressure chemical vapor deposition", T. Mikolajick, et. al., Fraunhofer Istitute Integrated Circuits Erlangen Germany, Sensors and Actuators B 44 (1997) 262-267

/3/ Sensitivity and hysteresis effect in $Al_2O_3$ gate pH-IS-FET, Jung-Chuan Chou et. al., National Yunlin University Taiwan, Materials Chemistry and Physics 71 (2001) 120-4

/4/ "Study of $TiO_2$ thin films for Ion Sensisitve Field Effect Transistor Application with RF sputtering deposition", Jung Chuan Chou, Lan Pin Liao, National Yunlin University of Science & Technology, Taiwan, Japanese Journal of Applied Physics 43, 1, 2004 pp. 61-65

/5/ "Development of a wide range pH sensor based on Elektrolyte-Insulator-Semiconductor structure with corrosion-resistant $Al_2O_3$—$Ta_2O_5$ and $Al_2O_3$—$ZrO_2$ double-oxide thin films", Shoji Yoshida, et. al., Tohoku University Sendai Japan, J. Electrochem. Soc. 151 (3) H53-H58 (2004)

/6/ "pH sensitivity improvement on 8 nm thick hafnium oxide by post deposition annealing", Chao-Sung Lai et. al., Chang Gung University Tao-Yuan Taiwan, Electrochemical and Solid-State Letters 9(3) G90-2 (2006)

/7/ J. G. Vlasov et. al., Journal Prikladnoi Chimi 61 (1988) 767-771

/8/ Dorota Sobczynska et. al., Sensors and Actuators 6 (1984) 93-105

/9/ U.S. Pat. No. 5,288,563

/10/ International Patent WO2005/073706

/11/ H. Remy, Lehrbuch der anorganischen Chemie, Band 1, 13.auflage, Akademische Verlagsgesellschaft Geest&Portig K.-G., Leipzig 1970

/12/ Jung-Chuan Chou, Chen-Yu Weng, Materials Chemistry and Physics 71 (2001) 120-124

/13/ Chao-Sung Lai et. al., Electrochemical and Solid-State Letters 9(3) G90-2 (2006)

/14/ Helmut Galster, "pH-Messung", VCH Weinheim 1990, S.108

/15/ M. Balog et. al., Thin Solid Films 41(1977)247-59

/16/ P. R. Chalker, et. al. Appl. Phys. Letters 93, 182911 (2008)

/17/ Yim Fun Loo et. Al., J. Appl. Phys. 99, 103704 (2006)

The invention claimed is:

1. An ion sensitive sensor having an electrolyte insulator semiconductor (EIS) structure, comprising:
   a semiconductor substrate, on which a layer of a substrate oxide is produced;
   an adapting or matching layer, which is prepared on said substrate oxide;
   a chemically stable, intermediate insulator, which is deposited on said adapting or matching layer; and
   an ion sensitive, sensor layer, which is applied on said intermediate insulator, wherein:
   said adapting or matching layer differs from said intermediate insulator and said substrate oxide in its chemical composition and/or structure;
   said adapting or matching layer and said ion sensitive, sensor layer each have an electrical conductivity greater than that of said intermediate insulator; and
   there is an electrically conductive connection between said adapting or matching layer and said ion sensitive, sensor layer.

2. The ion sensitive sensor as claimed in claim 1, wherein:
   said conductive connection extends in the direction of said layer sequence between said adapting or matching layer and said ion sensitive, sensor layer.

3. The ion sensitive sensor as claimed in claim 1, wherein:
   said conductive connection comprises especially the material of said adapting or matching layer, the material of said ion sensitive, sensor layer or a metal.

4. The ion sensitive sensor as claimed in claim 1, wherein:
   said intermediate insulator is surrounded laterally by a conductive intermediate layer, which forms the conductive connection extending between said adapting or matching layer and said ion sensitive, sensor layer.

5. The ion sensitive sensor as claimed in claim 1, wherein:
   said conductive connection comprises one or more conductive channels, which extend through said intermediate insulator.

6. The ion sensitive sensor as claimed in claim 1, wherein:
   said conductive connection is arranged in a lateral region of said ion sensitive sensor, which lies outside of the region, whose surface has said ion sensitive, sensor layer, and which is in contact with the measured medium.

7. The ion sensitive sensor as claimed in claim 1, wherein:
   said ion sensitive, sensor layer comprises tantalum oxide or tantalum oxynitride.

8. The ion sensitive sensor as claimed in claim 1, wherein:
   said intermediate insulator comprises hafnium oxide, zirconium oxide or a mixture of these oxides.

9. The ion sensitive sensor as claimed in claim 1, wherein:
   said sensor comprises an ion sensitive field effect transistor (ISFET) sensor.

10. The ion sensitive sensor as claimed in claim 1, wherein:
said adapting or matching layer comprises at least one material selected from the group of materials consisting of hafnium oxide silicate, zirconium oxide silicate, mixtures of hafnium oxide zirconium oxide silicate, hafnium oxynitride silicate, and zirconium oxynitride silicate, mixtures of hafnium oxynitride zirconium oxynitride silicate, hafnium oxide, tantalum oxide, tantalum oxynitride, and tantalum hafnium oxynitride, mixtures of tantalum hafnium oxide silicate, and mixtures of tantalum hafnium oxynitride silicate, hafnium lanthanum oxide, hafnium lanthanum oxynitride, hafnium ceroxide or hafnium cerium oxynitride.

11. The ion sensitive sensor as claimed in claim 1, wherein the substrate oxide has a layer thickness of 2.5 nm to 150 nm.

12. The ion sensitive sensor as claimed in claim 1, wherein:
said adapting or matching layer has a layer thickness of 1 nm to 135 nm.

13. The ion sensitive sensor as claimed in claim 1, wherein:
the intermediate insulator has a layer thickness of 20 nm to 200 nm.

14. The ion sensitive sensor as claimed in claim 1, wherein:
said sensor layer has a layer thickness of 10 nm to 200 nm.

15. The ion sensitive sensor as claimed in claim 1, wherein:
said substrate comprises silicon.

16. The ion sensitive sensor as claimed in claim 9, wherein:
said sensor comprises a pH ISFET sensor.

17. The ion sensitive sensor as claimed in claim 9, wherein:
said sensor comprises a light addressable potentiometric sensor (LAPS).

18. The ion sensitive sensor as claimed in claim 11, wherein the substrate oxide has a layer thickness of especially not less than 10 nm and no more than 90 nm.

19. The ion sensitive sensor as claimed in claim 12, wherein:
said adapting or matching layer has a layer thickness of especially not less than 5 nm and no more than 40 nm.

20. The ion sensitive sensor as claimed in claim 13, wherein:
the intermediate insulator has a layer thickness of especially not less than 30 nm and no more than 170 nm.

21. The ion sensitive sensor as claimed in claim 20, wherein:
the intermediate insulator has a layer thickness of preferably not less than 50 nm and no more than 150 nm.

22. The ion sensitive sensor as claimed in claim 14, wherein:
said sensor layer has a layer thickness of especially no more than 100 nm.

23. The ion sensitive sensor as claimed in claim 22, wherein:
said sensor layer has a layer thickness of preferably no more than 50 nm.

24. The ion sensitive sensor as claimed in claim 15, wherein:
said substrate comprises n-silicon.

* * * * *